Figure 1:
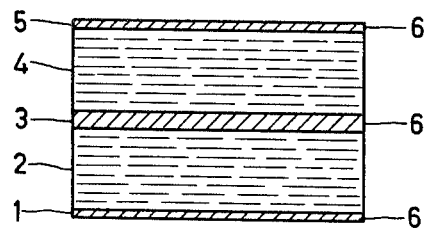

United States Patent [19]

Heijne

[11] 4,001,756
[45] Jan. 4, 1977

[54] MEASURING CELL FOR DETERMINING OXYGEN CONCENTRATIONS IN A GAS MIXTURE

[75] Inventor: Leopold Heijne, Eindhoven, Netherlands

[73] Assignee: U.S. Philips Corporation, New York, N.Y.

[22] Filed: July 23, 1975

[21] Appl. No.: 598,179

[30] Foreign Application Priority Data

Aug. 19, 1974 Netherlands ............... 7411044

[52] U.S. Cl. .............................. 338/34; 23/254 E;
73/27 R; 204/195 S; 324/71 SN; 338/325;
338/328; 357/25
[51] Int. Cl.² ............... H01L 31/00; G01N 31/00
[58] Field of Search ......... 23/254 E, 254 R, 232 R;
73/27 R; 338/34, 325, 328; 324/71 SN;
340/237 R; 204/195 S; 357/25

[56] References Cited

UNITED STATES PATENTS

| | | | |
|---|---|---|---|
| 2,711,511 | 6/1955 | Pietenpol | 324/71 SN |
| 2,720,573 | 10/1955 | Lundquist | 338/328 X |
| 2,975,362 | 3/1961 | Jacobson | 338/34 X |
| 3,250,966 | 5/1966 | Rose | 357/15 X |
| 3,321,681 | 5/1967 | Lauttman | 324/71 SN |
| 3,333,324 | 8/1967 | Roswell et al. | 357/15 |
| 3,334,248 | 8/1967 | Stratton | 357/15 |
| 3,428,892 | 2/1969 | Meinhard | 338/34 X |
| 3,558,280 | 1/1971 | Panson et al. | 23/254 E |
| 3,695,848 | 10/1972 | Taguchi | 73/27 R X |
| 3,879,985 | 4/1975 | Maslen | 338/34 X |

*Primary Examiner*—Morris O. Wolk
*Assistant Examiner*—Arnold Turk
*Attorney, Agent, or Firm*—Frank R. Trifari; Carl P. Steinhauser

[57] ABSTRACT

Measuring cell for determining oxygen concentrations in a gas mixture, which cell comprises two elements made of a semiconductive oxidic material which is doped so as to have n-type and p-type conductivity respectively and which are separated by a metal layer, the electric resistance of the said semiconductive oxide depending upon the oxygen pressure. The cell is used for carburation control in an internal combustion engine.

3 Claims, 5 Drawing Figures

MEASURING CELL FOR DETERMINING OXYGEN CONCENTRATIONS IN A GAS MIXTURE

The invention relates to a measuring cell for determining oxygen concentrations in a gas mixture.

Such a cell can also be used for measuring the carbon monoxide content in a gas mixture, because at low concentrations this carbon monoxide is in equilibrium with oxygen according to the equation $$CO + \tfrac{1}{2}O_2 \rightleftarrows CO_2.$$

In the combustion of organic fuel, such as coal, petroleum, petrol, natural gas, propane etc., the carbon dioxide content in the combustion gas has a given value so that there is a uniquely determined relation between the oxygen pressure and the carbon monoxide pressure.

An important use of the measuring cell according to the invention therefore is an apparatus in which the cell is placed in a flue of a combustion device, for example a space heating installation. Another important use is the insertion of the measuring cell in the exhaust pipe of an internal combustion engine. Such a device, which is extensively described in United Kingdom patent specification No. 1,306,844, includes a member for controlling the air/fuel ratio $\lambda$ and a feedback means acting on said member, causing the ratio $\lambda$ to be increased when the measuring cell indicates an increased content of CO or a reduced oxygen content.

Several types of measuring cells for determining oxygen concentrations are known.

One type has a partition made of a solid substance which has a reversible reaction with oxygen and in this reaction shows ion conductivity, such as stabilized zirconium oxide, the partition being coated with a thin metallic and/or semiconductive electrode layer on both major surfaces.

The gas mixture in which the partial oxygen pressure is to be measured is on one side of the partition on the other side of which a reference gas having a constant partial oxygen pressure is located. At a sufficiently high temperature, in practice at a temperature between 400° and 850° C, motion of the ions produces a potential difference E between the two electrodes which according to Nernst's equation $$E = \frac{RT}{2zF} \ln \frac{p_1}{p_2}$$

depends upon the ratio of the partial oxygen pressures $p_1$ and $p_2$. A disadvantage of a measuring cell of this type is that a reference atmosphere is required and that the cell may be sensitive to poisoning by given constituents of the combustion gas. Operation of a measuring cell of the known type is based on the dependence of the electric resistance of semiconductive oxides upon the partial oxygen pressure (See P. Kofstad, Non-stoichiometry, diffusion and electrical conductivity in binary metal oxides, Wiley-Interscience, New York 1972). A serious disadvantage of measuring cells of this type is that the resistance also greatly depends upon the temperature, so that the temperature of the cell must be kept exactly constant. In general the resistance of semiconductive oxide can be satisfactorily defined by the following formula

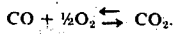

$$R(p,T) = 1\, R_o p^{\pm 1/n} \exp \frac{-A}{kT}$$

In this formula $R(p,T)$ is the resistance at the absolute temperature T and the partial oxygen pressure $p$, $R_o$ is a constant, $n$ is a number which for many substances lies between 4 and 6, $k$ is Boltzmann's constant and A is what is generally referred to as the activation energy. The latter quantity determines the degree of temperature dependence of the resistance. The plus sign in the formula applied to oxides having p-type conductivity, the minus sign to oxides having n-type conductivity.

We have tried to obtain an improved embodiment in which the temperature influence is compensated, by combining two identical measuring cells only one of which is exposed to the atmosphere to be analysed. Thus the temperature effects will compensate for one another. However, in this embodiment also the compensating measuring cell must be in contact with a constant reference atmosphere or at least the gas atmosphere to be measured must be completely excluded from it, which is particularly difficult at the high operating temperature and for the required long life.

According to the invention a combination of two measuring elements is used in which a semiconductive oxide having a pressure-dependent resistance is used which in one element is doped so as to have n-type conductivity and in the other is doped so as to have p-type conductivity, which elements are separated by a metal layer and together are exposed to the gas atmosphere to be analysed, while means are provided for measuring the resistance.

The oxides of p- and n-conductivity respectively which preferably contain the same basic oxide show equal but opposite pressure dependence. In the said combination these opposite resistance variations assist one another so that the output voltage varies with pressure by twice the amount which would be obtained with a single measuring element. In addition, the output voltage is substantially independent of temperature fluctuations in a range from 400° to 700° C. A reference atmosphere can be dispensed with. For resistance measurement a bridge circuit is preferably used.

The requirements an oxide must satisfy to be suitable for use in this construction are that by doping it can be given both n-type conductivity and p-type conductivity, that the activating energies of the two kinds of doped oxide preferably are about equal, and that the respective crystal lattice has a high diffusion coefficient for oxygen. The latter property is required to ensure a sufficiently high response rate at not too high an operating temperature.

A substance which well satisfies the said conditions is lead oxide at a temperature above 500° C, preferably the yellow modification, as described in a paper by L. Heijne, N. M. Beekmans and A. de Beer in J. Electrochem. Soc. 119, 77–84 (1972).

An embodiment of the invention will now be described, by way of example, with reference to the accompanying diagrammatic drawing.

Figure 2:
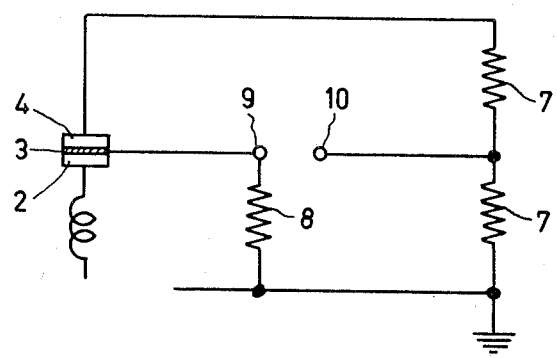
Figure 3:
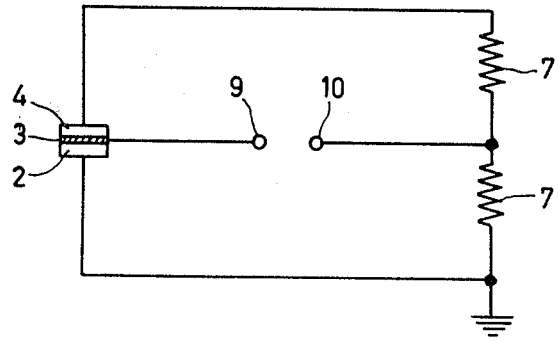
Figure 4:
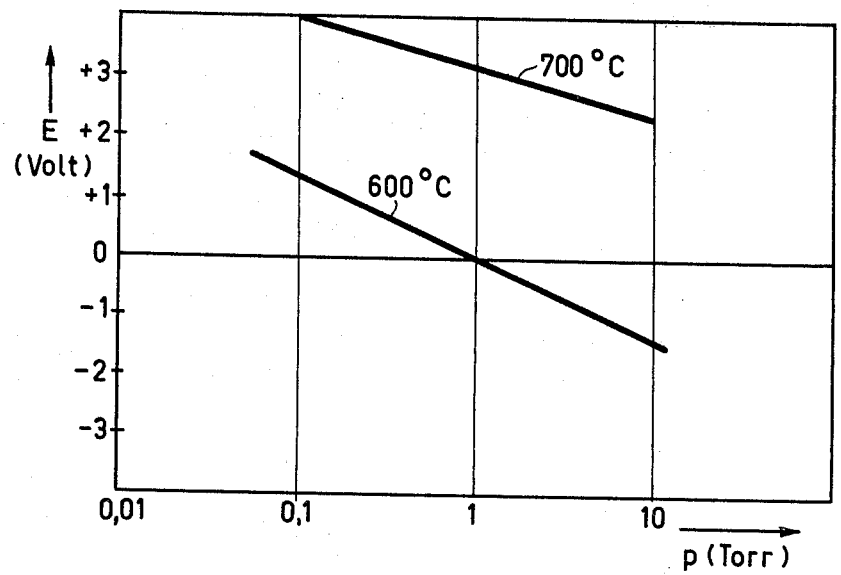
Figure 5:
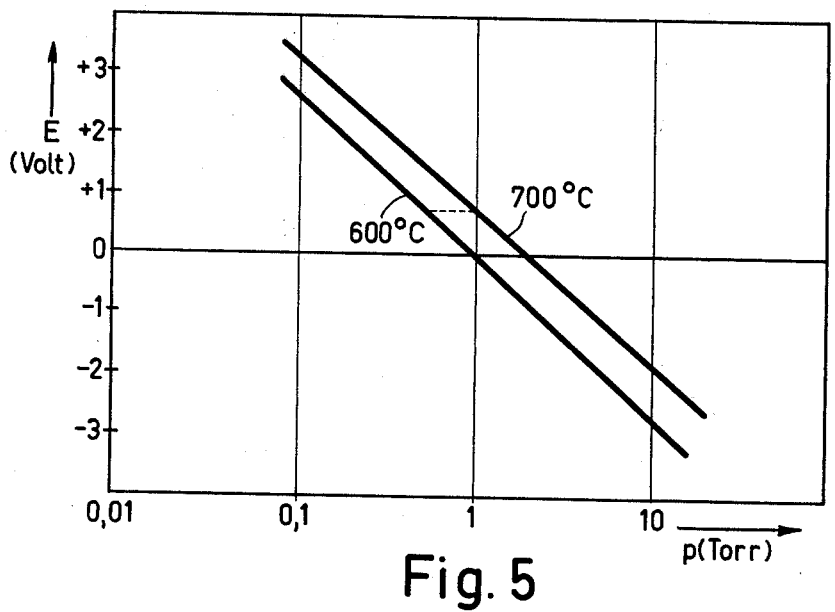

For manufacturing an oxygen measuring cell a circular platinum gauze 1, which afterwards is to be used as an electrode, is placed at the bottom of the cylindrical metal die of diameter 8 mm. 0.9 gram of a mixture of powdered lead oxide, 0.05 mole % of $K_2CO_3$ and 0.02 mole % of $SiO_2$ were introduced into the die and covered with a roughened disc of platinum foil 3. On this were placed 0.9 gram of another mixture of lead oxide and 0.005 mole % of $Bi_2O_3$. This was covered with a second platinum gauze 5. The assembly was compressed by a force of 6,000 kg. Thus a robust unit was obtained which could be removed from the die and then was further compressed by hydrostatic pressure under a pressure of 30,000 atmospheres. The combination was then sintered in air at 750° C for 8 hours, after which platinum wires 6 were secured to the three platinum electrodes. The resulting measuring cell had a diameter of about 8 mm and the two constituent lead oxide portions each were about 2 mm thick. FIG. 1 shows schematically the construction obtained. For testing as an oxygen measuring cell the assembly was placed in a furnace in which the gas atmosphere could be varied at will. The connecting wires were successively connected in the two circuits shown in FIGS. 2 and 3 respectively. The circuit of FIG. 2 is a bridge circuit which comprises two equal resistors 7, a fixed resistor 8 of 7,100 Ohms and the bismuth-doped part 4 of the measuring cell. In this circuit arrangement only the bismuth-doped section 4 of the device of the invention is included in this bridge circuit so that the device is made to operate in the manner of prior art devices in which the bridge unbalance current is determined by the change of the value of a resistance unit or a function of the oxygen pressure. However, in the arrangement of FIG. 3, the full capabilities of the device of the invention are utilized because both sections of the oxygen responsive device are contained in the bridge circuit which comprises in addition to the two lead-oxide parts 2–4 of the device of the invention, bridge resistors 7—7. In both circuits the bridge was fed with an alternating voltage of 10 Volts at a frequency of 50 Hz. The potential difference E between terminals 9 and 10 was measured as a function of the partial oxygen pressure at different temperatures. The potential difference between 9 and 10 was assigned a positive sign when it was in phase with the applied alternating voltage and a negative sign when it was in phase opposition to this supply voltage. The results obtained by means of the arrangement of FIG. 2 wherein only a single section 4 of the cell is used are shown in the diagram of FIG. 4. The voltage E measured is plotted along the vertical axis and the partial oxygen pressure is plotted along the horizontal axis on a logarithmic scale. Curves are given for the temperature 600° and 700° C. The Figure clearly shows that the temperature difference of 100° C gives rise to a very large error in the reading of the oxygen pressure. FIG. 5 shows the measurements of the arrangement according to the invention wherein both sections 2 and 4 of the cell are included in a circuit, also for the two temperatures 600° and 700° C, and the Figure shows that substantial compensation of the temperature influence has been obtained and that, as indicated by the steeper slopes of the lines, the sensitivity to pressure variations is increased. The residual temperature influence is due to the fact that the activating energies A of the lead oxide mixtures used for the two constituent parts are not exactly equal. For the bismuth-doped material of n-type conductivity an activating energy of 1.2 eV, for the potassium-doped part of p-type conductivity one of 0.9 eV was measured. For controlling combustion in an internal-combustion engine the compensation obtained will surely be sufficient in the case of a small excess of oxygen in the exhaust gas, for example at a partial oxygen pressure of 0.1 Torr. Obviously if more exacting requirements are to be satisfied a simple electrical compensation or a small extent of thermostatic control may be used. The oxygen pressure at which the output voltage is zero, in other words the set value for a coupled control system, can be adapted to a desired value by adapting the thickness or another dimension of the constituent parts. Owing to the high mobility of oxygen ions in lead oxide the response of the tested measuring cell was high. The most rapid oxygen pressure variations which could be brought about in the experimental arrangement used could immediately be followed by the measuring voltage E. From this it could be concluded that the response time was less than 1 second. A rapid response is promoted by making the constituent oxide layers thin.

The device according to the invention is obviously not restricted to lead oxide as the semi-conductive oxide. Many oxides, both binary and more complicated ones, show a dependence of the electric resistance on oxygen pressure at elevated temperatures. Manganese oxide is another example of a binary oxide which can have both n-type and p-type conductivity. Many other oxides can only be prepared either as n-type or as p-type semiconductors and then have the corresponding dependence on the oxygen pressure according to the above formula. Examples of binary oxides of n-type conductivity are $TiO_2$ and $CeO_2$, and examples of p-type oxides are NiO and CoO. Obviously the number of more complicated oxides, for example ternary oxides having spinel or perovskite structure, is far greater.

Obviously, to obtain the intended operation of a device according to the invention it is not necessary that the two oxidic semiconductor bodies connected in the bridge circuit be made of the same basic substance. An essential condition is only that they are of different conductivity types and that the thermal activating energies are well matched. The use of different basic substances provides an ample choice of making this matching as accurate as possible. In addition, matching may be optimized by variations in doping.

What is claimed is:

1. Measuring cell for determining oxygen concentrations in a gas mixture on the basis of a semiconductive oxide the electric resistance of which depends on the partial oxygen pressure, said cell comprising two measuring elements each comprising a semiconductive oxide, one element being doped to have n-type conductivity and the other being doped to have p-type conductivity, each of said elements having a high diffusion co-efficient for oxygen and having substantially equal activating energies, said elements being separated by a metal layer.

2. Measuring cell as claimed in claim 1, wherein the two measuring elements comprise the same oxide.

3. Measuring cell as claimed in claim 1 wherein the semiconductive oxide is yellow lead oxide.

* * * * *